US007319438B2

(12) United States Patent
Marino et al.

(10) Patent No.: US 7,319,438 B2
(45) Date of Patent: Jan. 15, 2008

(54) STABILIZATION OF THE EFFECTS OF JITTER ON A DISPLAYED IMAGE

(75) Inventors: Kenneth Marino, Oak Park, CA (US); Daniel A. Tazartes, West Hills, CA (US); Ragini Saxena, Simi Valley, CA (US)

(73) Assignee: Northrop Grumman Corporation, Los Angeles, CA (US)

( * ) Notice: Subject to any disclaimer, the term of this patent is extended or adjusted under 35 U.S.C. 154(b) by 582 days.

(21) Appl. No.: 10/991,066

(22) Filed: Nov. 17, 2004

(65) Prior Publication Data

US 2006/0114174 A1 Jun. 1, 2006

(51) Int. Cl.

| | |
|---|---|
| ***G09G 5/00*** | (2006.01) |
| ***G06F 3/038*** | (2006.01) |
| *G08G 5/04* | (2006.01) |
| *G01C 21/00* | (2006.01) |
| *G01C 9/00* | (2006.01) |
| *G01C 17/00* | (2006.01) |
| *G01C 19/00* | (2006.01) |
| *H04N 7/18* | (2006.01) |
| *A61M 21/00* | (2006.01) |

(52) U.S. Cl. .......................... 345/8; 340/961; 340/980; 345/7; 345/204; 348/148; 600/27; 702/150

(58) Field of Classification Search ..................... 345/8
See application file for complete search history.

(56) References Cited

U.S. PATENT DOCUMENTS

| | | | | |
|---|---|---|---|---|
| 4,390,950 | A * | 6/1983 | Muller | 701/4 |
| 6,348,877 | B1 * | 2/2002 | Berstis et al. | 340/980 |
| 7,128,705 | B2 * | 10/2006 | Brendley et al. | 600/27 |

* cited by examiner

*Primary Examiner*—Amare Mengistu
*Assistant Examiner*—Alexander S. Beck
(74) *Attorney, Agent, or Firm*—Carmen B. Patti & Assoc., LLC

(57) ABSTRACT

In an exemplary display system adapted to display an image to an observer using a display where at least one of the display and observer is subjected to physical vibration referred to as jitter, accelerometers are mounted to elements subject to jitter and associated with the observer. A processing system uses acceleration measurements from the accelerometers to calculate an x-axis and y-axis jitter correction factors based on a comparison of the acceleration measurements, and generates a video output in which the visual information is displaced along the x-axis and y-axis based on the x-axis and y-axis jitter correction factors so that an image corresponding to the video output shown on the display appears to the observer as not having jitter.

28 Claims, 1 Drawing Sheet

STABILIZATION OF THE EFFECTS OF JITTER ON A DISPLAYED IMAGE

BACKGROUND

This invention relates to the electronic display of an image and more specifically relates to compensating for undesired external physical movement (jitter) associated with a displayed image.

Environments exist in which significant jitter becomes associated with a displayed image. For example, a display system in a helicopter may display an image on a screen for the pilot where the image may include video information from a video camera, night vision viewing device, infrared viewing device, etc. mounted to the helicopter. In this relatively high vibration environment, the image displayed on the screen will be perceived by the pilot as having a substantial amount of jitter. There exists a need to minimize the perceived jitter of images displayed in a high vibration environment.

SUMMARY

In an embodiment of the invention, a display system is adapted to display an image to an observer using a display where at least one of the display and observer is subjected to physical vibration referred to as jitter. A first set of accelerometers is mounted to the display and a second set of accelerometers associated with the observer, such as mounted to a helmet worn by the observer. Each set of accelerometers comprises one or more accelerometers providing sensing of acceleration in one or more axes as appropriate. A processing system receives first and second sets of acceleration measurements from the first and second sets of accelerometers, respectively. A source of visual information provides the visual information to the processing system. The processing system calculates an x-axis and y-axis jitter correction factor based on a comparison of the first and second sets of acceleration measurements, generates a video output in which the visual information is displaced along the x-axis and y-axis based on the x-axis and y-axis jitter correction factors, respectively, and transmits the video output to the display so that an image corresponding to the video output shown on the display does not appear to the observer to be subject to jitter.

In another embodiment, the jitter correction factors are based on three sets of accelerometer measurements associated with the display, source of visual information and the observer where all are in an environment subject to jitter.

DETAILED DESCRIPTION

One of the aspects of the present invention resides in the recognition of the causes associated with jitter in display systems where multiple elements of the system are experiencing jitter. The source of jitter may come from jitter motion associated with the image capturing device, jitter motion associated with the screen itself on which the image is displayed, jitter motion associated with the head of the observer, or a combination thereof. For example, only compensating for jitter motion associated with the image capturing device relative to a fixed point of reference may be effective for some applications such as stabilizing images captured by a television camera undergoing jitter motion. Such compensation can be effective where the screen on which the image is displayed and the observer are not undergoing significant jitter motion. However, such compensation is not sufficient to present a satisfactory image to an observer where two or more elements in the display system (information source, display screen, observer) are each undergoing independent or semi-independent jitter motion. As explained with regard to the following description of an embodiment of the invention, compensation for jitter motion being experienced by multiple elements of the display system is provided in order to provide an image with minimized jitter from the perspective of the observer.

Figure 1:
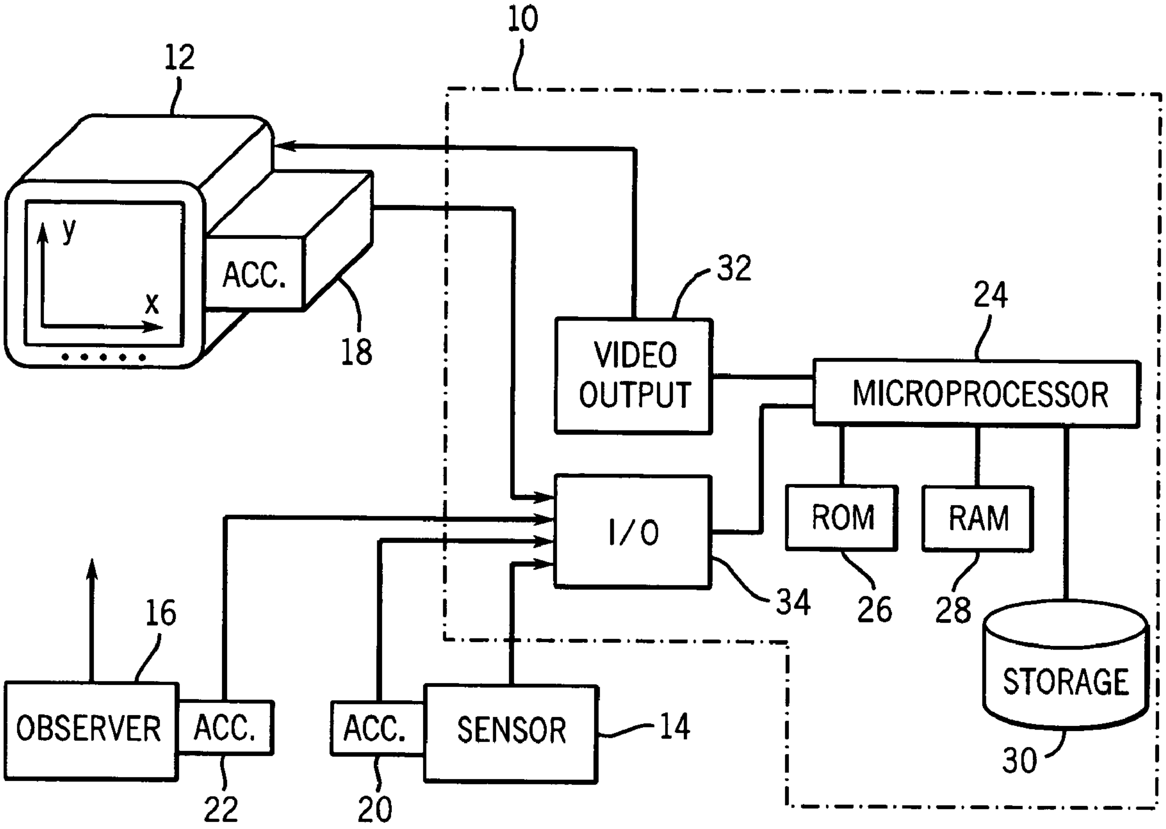
FIG. 1 is a block diagram illustrating an embodiment of a display system in accordance with the present invention in which jitter is minimized.

FIG. 1 illustrates a processing system 10 that provides a video signal to an electronic display 12 and receives information to be shown on the display from sensor 14. Display 12 can comprise any type of electronic video display and preferably is a video display that can accommodate screen rewrite rates of 30 Hz or higher, i.e. the ability to rewrite the screen at a rate at least faster than the ability of the human eye to follow each rewrite but preferably at a much higher rate, such as 300 Hz or higher. For example, an organic light emitting diode (OLED) display with rewrite times in the tens of microseconds would be suitable. The sensor 14 may comprise a video camera, other types of light sensors, or a sensor of other information where the visual presentation of the information can be adversely impacted by jitter motion of the sensor. The visually depicted information on display 12 is presented to an observer 16. In this illustrative example, the observer 16 may be a helicopter pilot, the monitor 12 may represent a display screen mounted to a console in the helicopter, and the sensor 14 may be a video camera mounted to the external fuselage of the helicopter for reconnaissance.

Accelerometers (or other inertial measurement units potentially also including gyroscopes) 18, 20 and 22 are mounted respectively to the display 12, sensor 14 and observer 16. The accelerometer 18 is adapted to provide two-dimensional acceleration measurements along the x-axis and y-axis as indicated on the screen of display 12. That is, the acceleration measurements correspond to acceleration in the plane of the screen of the display. Accelerometers 20 and 22 provide similar two-dimensional acceleration measurements, preferably along the same x-axis and y-axis as defined for accelerometer 18. The accelerometers 22 serves to monitor jitter motion associated with the observer, and in the illustrative example where the observer is a helicopter pilot, accelerometers 22 may be preferably mounted to the pilot's helmet or headset. It will also be appreciated that accelerometers 22 could be mounted to the pilot's seat, but would not provide acceleration measurements that would be as accurate as those provided by the accelerometers being, mounted as close as possible to track the motion of the head of the pilot. Each accelerometer set supplies an output containing two-dimensional acceleration information. In more sophisticated embodiments, a full inertial measurement unit comprising three axes of acceleration and angular rate sensing may be used in place of accelerometers 18, 20, and 22 to provide a 3 dimensional measurement of displacement at each of the three locations. These displacement measurements can then be projected in the appropriate plane for stabilization of the image.

The exemplary processing system 10 includes a microprocessor 24 that is supported by read-only memory (ROM) 26, random access memory (RAM) 28, and a nonvolatile data storage device 30 such as a hard drive. The microprocessor 24 is connected to a video output card 32 that supplies a video output signal to display 12. An input/output (I/O) interface device 34 is coupled to microprocessor 24 and receives acceleration measurements from accelerometers 18, 20 and 22. The interface device 34 also receives digital information from sensor 14 where the digital information is sent to the microprocessor 24 to be processed and forwarded to the video output device 32 for transmission to the display 12. The digital information may comprise digitized output from a video camera or other sensor.

The microprocessor 24 operates under stored program control instructions that may be stored in ROM 26 and/or storage device 30. As will be understood by those skilled in the art, microprocessor 24 performs a variety of conventional functions and tasks. In accordance with the exemplary embodiment, two-dimensional acceleration measurements from each of the accelerometers are periodically read and stored for use in jitter compensation calculations that are described in more detail in regard to FIG. 2. The microprocessor 24 processes the digital information received from sensor 14 and generates a modified video signal transmitted to video output card 32 that is based on the digital information received from sensor 14 and jitter compensation calculations.

Figure 2:
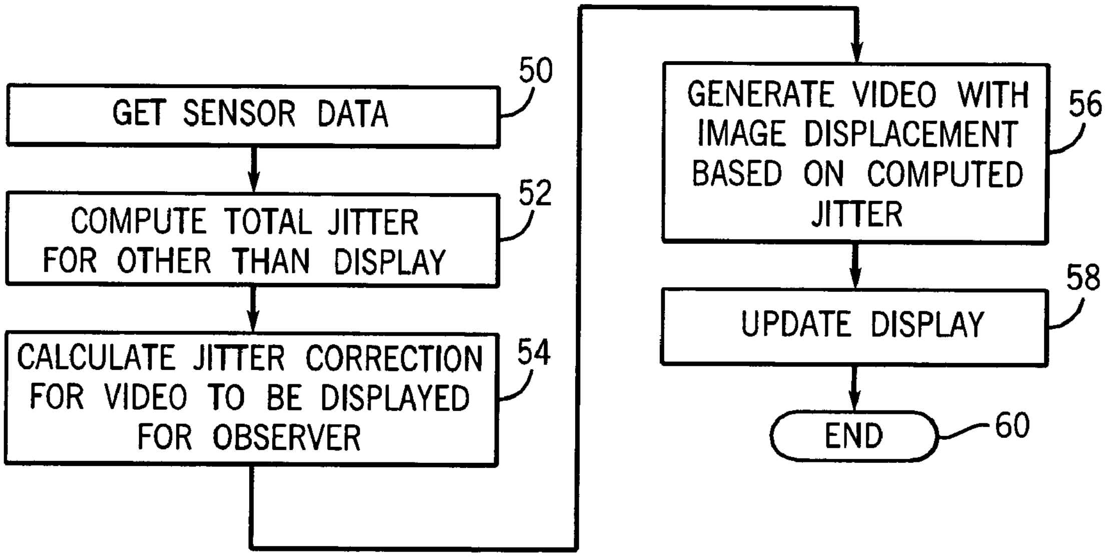
FIG. 2 is a flow diagram showing steps in an embodiment of an exemplary method in accordance with the present invention for minimizing jitter in a display system.

FIG. 2 illustrates a flow diagram showing steps in accordance with an exemplary method that may be practiced by the embodiment as shown in FIG. 1. In step 50 the acceleration measurements are periodically retrieved from each of the accelerometers. The rate at which the acceleration data is read is preferably equal to or greater than the rate at which the screen of the display 12 is to be refreshed. The total jitter as measured by all of the accelerometers, except for the accelerometer associated with the display, is computed in step 52. In the illustrative example, the total jitter is defined by adding the respective x-axis and y-axis acceleration measurements by accelerometers 20 and 22.

In step 54 x-axis and y-axis jitter correction factors are calculated to be applied in modifying the video to be displayed to the observer. The x-axis correction factor is calculated by comparing the total x-axis jitter with the x-axis acceleration measurements from accelerometer 18 representing the x-axis jitter associated with display 12. The difference between the total x-axis jitter and the x-axis jitter associated with display 12 is utilized to modify the placement of the image on the screen with regard to the x-axis. Linear displacement can be calculated using the well-known techniques such as double integration of the acceleration. An approximation for linear displacement may also comprise an equation in which displacement is proportional to acceleration multiplied by time squared (assuming the velocity component is zero or small enough to be ignored as in the illustrative example). Thus, the distance to shift the image to be displayed along the x-axis to stabilize the image from the perspective of the observer can be computed based on the x-axis correction factor processed to yield an image displacement value. This will result in the projection of the image at a location along the x-axis so as to appear stationary or not having moved due to jitter from the perspective of the observer. The y-axis correction factor is calculated similarly in order to determine the amount, if any, that the image should be shifted in the y-axis so as to appear stabilized from the perspective of the observer. Filters (in particular high-pass or band-pass filters) may be applied to the either the acceleration measurements or to the displacement value in order to ensure that corrections are only applied for high frequencies and not for motions resulting from actual maneuvers of the vehicle. In this way the correction accounts for jitter but does not negate a change in position of an object shown in the image where the observer is deliberately moving with respect to the object. The filter characteristics are to be chosen depending on the characteristics of the vehicle, the frequency bands of the jitter motion, and the frequency bands where image jitter suppression is desirable.

In step 56 modified video is generated by the microprocessor based on the video information received from the sensor 14 and the x-axis and y-axis correction factors. The video information to be transmitted to the video output card 32 is modified so that the video information output from the video output card 32 to display 12 will be shifted on the screen based on the computed x-axis and y-axis correction factors. In step 58 display 12 is updated with a new frame of video information that has been modified with appropriate x-axis and y-axis image shifting so that undesired external jitter is neutralized from the perspective of observer 16. This process terminates at END 60. It will be understood that x-axis and y-axis correction factors are preferably computed for each frame of video (or more frequently if acceleration information is updated more often than for each video frame) and are utilized to generate a shifted image during each frame.

Although an embodiment of the present invention has been described, it will be apparent to those skilled in the art that various changes and alterations can be made to the embodiment without departing from the present invention. Depending upon the specific environment, it may be possible to provide adequate image stabilization based on only two different sources of acceleration measurements. For example, assuming a helicopter environment in which the observer is the pilot and the display is mounted to a console in the helicopter that is in motion, a land-based video camera (having no substantial jitter) may be wirelessly transmitted to the helicopter to be displayed. In this situation acceleration measurements would only be required for display 12 and the observer 16 since no significant jitter would be introduced by the sensor 14, the land-based video camera. Video, in addition to being real-time image information, may comprise a stored image such as a chart, graph, map, or picture. Although the processing system 10 is shown as a separate device such as a computer or work station, the steps of the exemplary method could be performed in a computing environment that may already exist to perform other functions including integration of the method into the display itself. The acceleration measurement data could be integrated for transmission with other information. These modifications are merely intended to suggest some of the possible modifications. The scope of the invention is defined by the following claims.

What is claimed is:

1. A display system adapted to display an image to an observer comprising:

a display;

at least one of the display and observer being subjected to physical vibration referred to as jitter;

a first accelerometer mounted to the display;

a second accelerometer associated with the observer;

a processing system that receives first and second acceleration measurements from the first and second accelerometers, respectively;

a source of visual information adapted to provide the visual information to the processing system;

the processing system adapted to:

calculate an x-axis and y-axis jitter correction factor based on a comparison of the first and second acceleration measurements, generate a video output in which the visual information is displaced along the x-axis and y-axis based on the x-axis and y-axis jitter correction factors, respectively, and transmit the video output to the display so that an image corresponding to the video output shown on the display does not appear to the observer to be subject to jitter.

2. The display system of claim 1 wherein the display has a screen that can be rewritten at a rate of 30 Hz or higher.

3. The display system of claim 1 wherein the first and second accelerometers each provide x-axis and y-axis acceleration measurements.

4. The display system of claim 1 wherein the processing system calculates the jitter correction factors by comparing a first acceleration measurement with a second acceleration measurement to determine an x-axis and y-axis acceleration differential that is processed to estimate a corresponding displacement on the x-axis and y-axis.

5. The display system of claim 1 wherein at least one of the display and source of visual information are subjected to jitter, the observer is subjected to jitter, and the display system further comprises a third accelerometer mounted to the source of visual information.

6. The display system of claim 1 wherein the display, source of visual information and the observer are all subjected to jitter, and the display system further comprises a third accelerometer mounted to the source of visual information.

7. The display system of claim 6 wherein the processing system calculates the x-axis and y-axis jitter correction factors based on a comparison of the first acceleration measurement to one of the second acceleration measurement, third acceleration measurement, and a combination of the second and third acceleration measurements.

8. The display system of claim 7 wherein the processing system calculates the jitter correction factors by comparing a first acceleration measurement with said one to determine an x-axis and y-axis acceleration differential that is processed to estimate a corresponding displacement on the x-axis and y-axis.

9. The display system of claim 8 wherein the display has a screen that can be rewritten at a rate of 30 Hz or higher.

10. The display system of claim 8 wherein the first, second and third accelerometers each provide x-axis and y-axis acceleration measurements.

11. The display system of claim 1 wherein the second accelerometer is mounted to a helmet worn by the observer.

12. A method for minimizing jitter as an observer views an image on a screen of a monitor in a display system where at least some elements associated with the display system is in an environment subject to jitter comprising the steps of:

receiving a first accelerometer measurement associated with the observer and at least a second accelerometer measurement associated with an element of the display system that is in an environment subject to jitter, the first and second accelerometer measurements each containing x-axis and y-axis acceleration information;

receiving a visual information signal;

calculating x-axis and y-axis jitter correction factors based on a comparison of the x-axis and y-axis acceleration information from the first and second accelerometer measurements;

generating a video output signal in which the visual information contained in the visual information signal is displaced along the x-axis and y-axis based on the x-axis and y-axis jitter correction factors, respectively;

transmitting the video output signal to the display so that an image corresponding to the video output signal is shown on the display so as to appear to the observer as not containing jitter.

13. The method of claim 12 further comprising receiving second and third accelerometer measurements associated with the monitor and a source of visual information that are both in an environment subject to jitter.

14. The method of claim 13 wherein the calculating of the x-axis and y-axis jitter correction factors are based on a comparison of the x-axis and y-axis acceleration information of the first accelerometer measurement with the cumulative of the x-axis and y-axis acceleration information from the second and third accelerometer measurements, respectively.

15. The method of claim 12 wherein the first accelerometer measurement is associated with the observer by utilizing an accelerometer mounted to a helmet worn by the observer.

16. An article comprising:

one or more computer-readable signal-bearing media;

means in the one or more media for receiving a first accelerometer measurement associated with an observer and at least a second accelerometer measurement associated with an element of a display system that is in an environment subject to jitter, the first and second accelerometer measurements each containing x-axis and y-axis acceleration information;

means in the one or more media for receiving a visual information signal;

means in the one or more media for calculating x-axis and y-axis jitter correction factors based on a comparison of the x-axis and y-axis acceleration information from the first and second accelerometer measurements;

means in the one or more media for generating a video output signal in which the visual information contained in the visual information signal is displaced along the x-axis and y-axis based on the x-axis and y-axis jitter correction factors, respectively;

means in the one or more media for transmitting the video output signal to the display so that an image corresponding to the video output signal is shown on the display so as not to appear to the observer as containing jitter.

17. The article of claim 16 further comprising means in the one or more media for receiving second and third accelerometer measurements associated with the monitor and a source of visual information that are both in an environment subject to jitter.

18. The article of claim 17 wherein the calculating of the x-axis and y-axis jitter correction factors are based on a comparison of the x-axis and y-axis acceleration information of the first accelerometer measurement with the cumulative of the x-axis and y-axis acceleration information from the second and third accelerometer measurements, respectively.

19. The article of claim 16 wherein the first accelerometer measurement is obtained from an accelerometer mounted to a helmet worn by the observer.

20. The display system of claim 1 wherein the processing system is adapted to transmit the video output to the display so that an image corresponding to the video output shown on the display does not appear to the observer to be subject to jitter within a predetermined frequency band of the jitter.

21. A display system adapted to display an image to an observer comprising:

a display;

at least one of the display and observer being subjected to physical vibration referred to as jitter;

a first inertial measurement unit mounted to the display;

a second inertial measurement unit associated with the observer;

a processing system that receives first and second acceleration measurements from the first and second inertial measurement units, respectively;

a source of visual information adapted to provide the visual information to the processing system;

the processing system:

calculates an x-axis and y-axis jitter correction factor based on a comparison of the first and second inertial measurement unit position measurements, generates a video output in which the visual information is displaced along the x-axis and y-axis based on the x-axis and y-axis jitter correction factors, respectively, and transmits the video output to the display so that an image corresponding to the video output shown on the display does not appear to the observer to be subject to jitter within a predetermined frequency band of interest.

22. The display system of claim 21 wherein the display has a screen that can be rewritten at a rate of 30 Hz or higher.

23. The display system of claim 21 wherein the first and second inertial measurement units each provide x-axis and y-axis position and attitude measurements.

24. The display system of claim 21 wherein the processing system calculates the jitter correction factors by comparing a first position measurement with a second position measurement to determine an x-axis and y-axis position differential that is processed and filtered to estimate a corresponding displacement on the x-axis and y-axis within the frequency band of interest.

25. The display system of claim 21 wherein at least one of the display and source of visual information are subjected to jitter, the observer is subjected to jitter, and the display system further comprises a third inertial measurement unit mounted to the source of visual information.

26. The display system of claim 21 wherein the display, source of visual information and the observer are all subjected to jitter, and the display system further comprises a third inertial measurement unit mounted to the source of visual information.

27. The display system of claim 25 wherein the processing system calculates the x-axis and y-axis jitter correction factors based on a comparison of the first position measurement to one of the second position measurement, third position measurement, and a combination of the second and third position measurements.

28. The display system of claim 27 wherein the processing system calculates the jitter correction factors by comparing a first position measurement with the one measurement to determine an x-axis and y-axis acceleration differential that is processed to estimate a corresponding displacement on the x-axis and y-axis within the frequency band of interest.

* * * * *